United States Patent [19]

Ohya et al.

[11] Patent Number: 5,691,451
[45] Date of Patent: Nov. 25, 1997

[54] METHOD FOR STERILIZING RECOMBINANT HUMAN SERUM ALBUMIN PHARMACEUTICAL PREPARATION

[75] Inventors: Tomoshi Ohya; Toyoo Ohda; Shinobu Kuwae; Kenji Tomomitsu; Kaoru Kobayashi; Takao Ohmura, all of Osaka, Japan

[73] Assignee: The Green Cross Corporation, Osaka, Japan

[21] Appl. No.: 329,176

[22] Filed: Oct. 26, 1994

[30] Foreign Application Priority Data

Oct. 27, 1993 [JP] Japan .................. 5-269168

[51] Int. Cl.$^6$ .................. C07K 1/00; C12P 21/06
[52] U.S. Cl. .................. 530/363; 530/362; 530/364; 435/69.1; 435/69.6; 435/70.1; 435/71.1
[58] Field of Search .................. 530/363, 362, 530/364; 435/69.1, 69.6, 70.1, 71.1

[56] References Cited

U.S. PATENT DOCUMENTS

| | | | |
|---|---|---|---|
| 4,849,508 | 7/1989 | Magnin et al. | 530/387.1 |
| 5,118,794 | 6/1992 | Grangeorge et al. | 530/363 |
| 5,132,404 | 7/1992 | Ohtani et al. | 530/364 |
| 5,294,699 | 3/1994 | Ohmumura et al. | 530/364 |
| 5,334,512 | 8/1994 | Kobayashi et al. | 435/69.6 |
| 5,369,020 | 11/1994 | Suni et al. | 435/69.6 |

FOREIGN PATENT DOCUMENTS 0341103  11/1989  European Pat. Off. .

OTHER PUBLICATIONS

Dengler et al, *Chemical Abstracts*, vol. 112, p. 274, Ref. #118203. 1990 (Infusiontherapie, 1989, 16(4), 160–164).

*Primary Examiner*—Cecilia J. Tsang
*Assistant Examiner*—Abdel A. Mohamed
*Attorney, Agent, or Firm*—Sughrue, Mion, Zinn, Macpeak & Seas, PLLC

[57] ABSTRACT

A recombinant human serum albumin (rHSA) pharmaceutical preparation is sterilized by subjecting a pharmaceutical preparation of rHSA obtained by gene manipulation techniques packed in a container in an administration unit to heat treatment at 50° to 80° C. for 30 minutes or more. By the disclosed method, rHSA having high safety can be provided since microorganisms contaminated in rHSA pharmaceutical preparations die as a result of the sterilization method of the present invention.

6 Claims, No Drawings

METHOD FOR STERILIZING RECOMBINANT HUMAN SERUM ALBUMIN PHARMACEUTICAL PREPARATION

FIELD OF THE INVENTION

This invention relates to a method for the sterilization of various microorganisms contaminated in pharmaceutical preparations of recombinant human serum albumin obtained by gene manipulation techniques.

BACKGROUND OF THE INVENTION

In the case of human serum albumin (to be referred to as "HSA" hereinafter) preparations derived from blood plasma, the danger of viral contamination becomes extremely high when the preparations produced using blood material collected from a virus infected blood donor. To inactivate viruses that contaminate plasma-derived pharmaceutical preparations, several processes have been proposed, which are, for example, a process in which a compound such as β-propiolactone is used jointly with UV ray irradiation, a process in which a mixed solution of an organic solvent and a surface active agent is used, and a process in which heat treatment is employed.

However, joint use of a compound and UV irradiation may possibly cause changes in the correct antigenicity of the pharmaceutical preparation, and a drawback of using a mixed solution of an organic solvent and a surface active agent is that the process is limited to the inactivation of lipid-enveloped viruses.

Heat treatment is generally carried out by low temperature disinfection (pasteurization), which does not spoil the quality of the pharmaceutical preparation, and is employed in the final step of the plasma-derived HSA pharmaceutical production process. With regard to HSA pharmaceutical preparations, it has been reported that the hepatitis virus can be inactivated by 10 hours of heat treatment at 60° C. (pasteurization), and the thermal stability of albumin during heat treatment for inactivating proteases which degrade HSA can be ensured by the addition of a stabilizing agent, such as sodium acetyl tryptophan, a fatty acid salt or the like (U.S. Pat. No. 5,132,404). The inactivation effect of pasteurization under the same conditions as above has also been reported in the case of other viruses that may possibly contaminate blood preparations. Biological product standards prescribe that pasteurization should be carried out at 60.0±0.5° C. for 10 hours or more when plasma-derived HSA is produced.

On the other hand, pharmaceutical preparations of recombinant human serum albumin (to be referred to as "rHSA" hereinafter) obtained by gene manipulation techniques have an extremely low possibility of causing viral contamination, because material having a possibility of containing viruses is not used. The possibility of causing microbial contamination during production of the pharmaceutical preparation is also extremely low, because the preparation is subjected to sterile filtration at the final step and then dispensed and packed aseptically. However, in order to more positively ensure sterility of the rHSA pharmaceutical preparation to further improve its safety, it is advantageous to subject rHSA, which has been packed in a container in an administration unit, to a final sterilization treatment. No technique has been known so far to sterilize recombinant HSA by heat treatment.

SUMMARY OF THE INVENTION

An object of the present invention is to provide a method for the sterilization of a rHSA pharmaceutical preparation under the specific condition in which rHSA is packed in a container in an administration unit.

The inventors of the present invention have hypothesized various microorganisms that may possibly be present as contaminants after aseptic packing of a pharmaceutical preparation of rHSA obtained by gene manipulation techniques, and, in order to determine conditions for their sterilization, conducted intensive studies on the pasteurization inactivation of these microorganisms by changing the time period for pasteurization occurring at around 60° C. The present invention has been accomplished on the basis of these efforts.

Accordingly, the present invention relates to a method for sterilizing a recombinant human serum albumin pharmaceutical preparation, comprising subjecting a pharmaceutical preparation of recombinant human serum albumin obtained by gene manipulation techniques, which is packed in a container in an administration unit, to heat treatment at 50° to 80° C. for 30 minutes or more.

Other objects and advantages of the present invention will be apparent from the following detailed description and examples.

DETAILED DESCRIPTION OF THE INVENTION

I. Production of rHSA pharmaceutical preparation obtained by gene manipulation techniques (1) Preparation and culturing of HSA producing host cells and isolation and collection of HSA The origin of the starting recombinant HSA used in the instant invention is not limited, provided, however, the HSA is prepared by gene manipulation techniques. The HSA-producing host to be used in the instant invention is not limited, provided, however, it is prepared by gene manipulation techniques. Hence the host can be selected from hosts already reported in publications, as well as those hosts that will be developed in the future. Illustrative examples of the host include microbial cells, such as *Escherichia coli*, various yeast species, *Bacillus subtilis*, and animal cells, which have been made into HSA producers. Particularly preferred hosts are yeast species, especially those belonging to the genus Saccharomyces, such as *Saccharomyces cerevisiae*, the genus Pichia, such as *Pichia pastoris* or the genus Kluyveromyces, such as *Kluyveromyces lactis*. Auxotrophic strains or antibiotic-sensitive strains also may be used. *Saccharomyces cerevisiae* AH22 (a, his 4, leu 2, can 1), *Pichia pastoris* GTS115 (his 4) and *Kluyveromyces lactis* MW-98-8C (α, uraA, arg, lysK$^+$, pKD1°) are used preferably. The HSA used in the instant invention is preferably produced using these hosts.

Preparation of the HSA-producing hosts, production of HSA by culturing the hosts, and isolation and recovery of HSA from the resulting culture broth may be effected using known techniques or modified procedures thereof.

For example, preparation of an HSA-producing host (or an HSA-producing strain) may be effected using a process in which a natural human serum albumin gene is used (JP-A-58-56684 corresponding to EP-A-73646, JP-A-58-90515 corresponding to EP-A-79739 and JP-A-58-150517 corresponding to EP-A-91527), a process in which a modified human serum albumin gene is used (JP-A-62-29985 and JP-A-1-98486 corresponding to EP-A-206733), a process in which a synthetic signal sequence is used (JP-A-1-240191 corresponding to EP-A-329127), a process in which a serum albumin signal sequence is used (JP-A-2-167095 corresponding to EP-A-319641), a process in which a recombinant plasmid is introduced into a chromosome (JP-A-3-72889 corresponding to EP-A-399455), a process in which hosts are fused (JP-A-3-53877 corresponding to EP-A-409156), a process in which a mutation is generated in a methanol containing medium, a process in which a mutant AOX2 promoter is used (EP-A-506040), a process in which HSA is expressed in *B. subtilis* (JP-A-62-215393 corresponding to EP-A-229712), a process in which HSA is expressed in yeast (JP-A-60-41487 corresponding to EP-A-123544, JP-A-63-39576 corresponding to EP-A-248657 and JP-A-63-74493 corresponding to EP-A-251744) and a process in which HSA is expressed in Pichia (JP-A-2-104290 corresponding to EP-A-344459).

Culturing of an HSA-producing host (an HSA production process) may be carried out using known processes disclosed in the above-mentioned references; or in accordance with a process disclosed in JP-A-3-83595, in which high concentration substrate inhibition of HSA producer cells is avoided by gradually adding a high concentration glucose solution to the medium by means of fed batch fermentation, thereby enabling production of both the producer cells and the product in high concentrations; or in accordance with another process disclosed in JP-A-4-293495 corresponding to EP-A-504823, in which productivity of HSA is improved by adding fatty acids to the medium.

Isolation and recovery of HSA may be carried out using known processes disclosed in the above-mentioned references, or in accordance with a process disclosed in JP-A-3-103188 corresponding to EP-A-420007, in which proteases are inactivated by heat treatment; or a coloration inhibition process disclosed in JP-A-4-54198 corresponding to U.S. Pat. No. 5,132,404 or EP-A-464590, in which HSA is separated from coloring substances using at least one adsorbent selected from the group consisting of anion exchangers, hydrophobic carriers and activated charcoal.

(2) Initial purification of HSA

The HSA can be initially purified by known methods, such as fractionation, adsorption chromatography, gel filtration, density-gradient centrifugation or dialysis.

A suitable initial purification method contains the following steps:
(i) passing a culture supernatant of a host that expresses HSA, through a first ultrafiltration membrane having a molecular weight exclusive limit of from 100,000 to 500,000 and then through a second ultrafiltration membrane having a molecular weight exclusive limit of from 1,000 to 50,000 to yield a first filtrate;
(ii) heat-treating the first filtrate at 50° to 70° C. for 30 minutes to 5 hours to yield a heated sample;
(iii) acid-treating the heated sample at a pH of from 3 to 5 to yield an acid-treated sample;
(iv) passing the acid-treated sample through ultrafiltration membrane having a molecular weight exclusive limit of from 100,000 to 500,000 to yield a second filtrate;
(v) exposing the second filtrate to a cation exchanger, at a pH of 3 to 5 and a salt concentration of 0.01 to 0.2M, and then exposing said cation exchanger to a pH of 8 to 10 and a salt concentration of 0.2 to 0.5M to yield a first eluate;
(vi) allowing the first eluate to contact a carrier for hydrophobic chromatography at a pH of 6 to 8 and a salt concentration of 0.01 to 0.5M, and recovering non-adsorbed fractions to yield a second eluate; and
(vii) allowing the second eluate to contact an anion exchanger at a pH of 6 to 8 and a salt concentration of 0.01 to 0.1M, and recovering non-adsorbed fractions to yield said albumin.

Alternatively, instead of the aforementioned step (vi), an alternative step may be employed in which the corresponding sample is allowed to contact with a hydrophobic chromatography carrier at pH 6 to 8 with a salt concentration of 1 to 3M and subsequently eluted at pH 6 to 8 with a salt concentration of 0.01 to 0.5M; instead of the aforementioned step (vii), an alternative step may be employed in which the corresponding sample is allowed to contact with an anion exchanger at pH 6 to 8 with a salt concentration of 0.01 to 0.05M and subsequently eluted at pH 6 to 8 with a salt concentration of 0.05 to 1M; or an additional step in which salting out is effected at pH 3 to 5 with a salt concentration of 0.5 to 3M and the precipitated fraction is recovered may be introduced between the aforementioned steps (v) and (vi), or (vi) and (vii), or after (vii).

(3) High grade purification

The following treatments may be carried out in order to purify HSA to a high degree.

(i) Decoloration of HSA

The above HSA purification steps may further contain a decoloration step, preferably as a final step, which is carried out by allowing HSA to contact with a chelate resin that has a specified ligand moiety. Preferably, the carrier moiety of the chelate resin will have a hydrophobic nature. Examples of such a type of carrier moiety include a copolymer of styrene and divinylbenzene, a copolymer of acrylic acid and methacrylic acid.

Examples of the ligand moiety include a thiourea group, as well as a polyamine group (including a polyalkylene polyamine group, such as polyethylene polyamine) which contains, in one molecule, a plurality of sub-groups consisting of a polyol group, such as an N-methylglucamine group, an imino group, an amino group, an ethyleneimino group. Illustrative examples of preferred commercially available chelate resins having the above-described carrier and ligand moieties, include DIAION CRB02 (ligand moiety, N-methylglucamine group, available from Mitsubishi Kasei Corp.), DIAION CR20 (ligand moiety, —NH(CH$_2$CH$_2$NH)$_n$H, available from Mitsubishi Kasei Corp.), LEWATIT TP214 (ligand moiety, —NHCSNH$_2$, available from Bayer) and AMBERLITE CG4000, all of which have a copolymer of styrene and divinylbenzene as the carrier moiety.

Preferred conditions for the chelate resin treatment are as follows.

pH: acidic or neutral (pH 3 to 9, preferably 4 to 7),
period: at least 1 hour, preferably 6 hours or more,
ionic strength: 50 mmho or less, preferably 1 to 10 mmho,
mixing ratio: 0.1 to 100 g, preferably 1 to 10 g, of the resin based on 250 mg of HSA (wet basis).

(ii) Hydrophobic chromatography

Free nonantigenic contaminants detectable by the phenol-sulfuric acid method are not fully removed from the HSA obtained through the above-described purification steps (i) to (vii) and the chelate resin treatment.

The HSA obtained through the above-described treatments is allowed to contact a carrier for hydrophobic chromatography at a pH of 2 to 5, preferably 3 to 4 and a salt concentration of 0.4 to 1M, preferably 0.4 to 0.7M. The elution can be effected at a pH of 6 to 8, preferably 6.5 to 7 and a salt concentration of 0.01 to 0.3M, preferably 0.05 to 0.2M. The above-described step (vi) may be replaced with this hydrophobic chromatography step. Thus, HSA which does not contain free nonantigenic contaminants detectable by the phenol-sulfuric acid method can be recovered.

The term "phenol-sulfuric acid treatment" used herein means the colorimetric determination of carbohydrates which comprises adding a phenol solution to a sample carbohydrate solution, adding concentrated sulfuric acid thereto, shaking the mixture to allow a furfural derivative derived from the carbohydrate utilizing heat of dissolution to react with phenol, and colorimetrically determining the resulting colored reaction product. The free nonantigenic contaminants detectable by the phenol-sulfuric acid method include neutral carbohydrates, such as pentose and hexose, monocarbohydrate glycoside, such as oligosaccharides, complex carbohydrates and uronic acid, methylated carbohydrate. These contaminants do not cause antigen-antibody reaction with antibodies against producer host-derived substances.

Carriers for use in hydrophobic chromatography include those containing an alkyl group (butyl group, octyl group, octyldecyl group and the like), each group having 4 to 18 carbon atoms, and those containing a phenyl group. Illustrative examples of the butyl group-containing carriers include butyl-agarose, butyl-polyvinyl (trade name, Butyl Toyopearl, available from Tosoh Corp.), those of the octyl group-containing and octyldecyl group-containing carriers include octyl-agarose and octyldecyl-agarose, respectively, and those of the phenyl group-containing carrier include phenyl-cellulose (trade name, Phenyl Cellulofine, available from Seikagaku Corp.).

(iii) Treatment with boric acid or a salt thereof

HSA can be treated with boric acid or a salt thereof to remove antigenic producer host-derived contaminants as well as free nonantigenic contaminants detectable by the phenol-sulfuric acid method.

Examples of the boric acid include orthoboric acid, metaboric acid, tetraboric acid. The salts thereof include alkali metal salts such as sodium salt and potassium salt, alkaline earth metal salts such as calcium salt. Calcium tetraborate is preferably used. Boric acid or a salt thereof is added to a final concentration of about 0.01 to 1M, preferably about 0.05 to 0.2M. This treatment can be carried out at a pH of about 8 to 11, preferably about 9 to 10 for about 1 to 10 hours. This treatment is preferably effected at a low electric conductivity, for example, 1 mS or less. The HSA concentration is preferably low, for example, 5% or less, more preferably about 0.1 to 3%.

After the treatment with boric acid or a salt thereof, the precipitate formed is removed by, for example, centrifugation or filtration and the supernatant is recovered, concentrated and desalted.

(iv) Ultrafiltration

The HSA recovered after the above purification steps is preferably subjected to ultrafiltration using an ultrafiltration membrane having a molecular weight exclusive limit of about 100,000. Pyrogen can be removed by this ultrafiltration treatment.

(v) Properties of purified HSA (rHSA)

The HSA isolated and purified through the above steps is a homogeneous substance having a molecular weight of about 67,000 and an isoelectric point of 4.6 to 5.0. The HSA consists of a monomer and contains substantially no dimers, polymers or decomposed products. In fact, the total content of dimers, polymers and hydrolyzed products is approximately 0.01% or less. Also, the HSA of the instant invention contains substantially no producer host-derived contaminants, such as protein, polysaccharide, that is, no contaminants having antigenicity. In the case of a 25 w/v % HSA solution, the content of the contaminants may be 1 ng/ml or below, preferably 0.1 ng/ml or below, and the polysaccharide content may be 1 ng/ml or below, preferably 0.1 ng/ml below. In that case, the purity of the HSA is calculated to be 99.999999% or more, preferably 99.9999999% or more. The degree of coloring of the 25 w/v % HSA solution may be in the range of from 0.01 to 0.05 in terms of an $A_{350}/A_{280}$ ratio, from 0.001 to 0.02 as an $A_{450}/A_{280}$ ratio and from 0.001 to 0.005 as an $A_{500}/A_{280}$ ratio. In addition, the amount of fatty acids linked to the HSA may be one molecule or less, preferably 0.1 molecule or less, per one HSA molecule.

Particularly, the HSA of the present invention is characterized in that it contains, per 250 mg of the HSA, (a) 0.1 ng or less of contaminants having host-derived antigenicity, (b) 1 mg or less of nonantigenic free contaminants detectable by the phenol-sulfuric acid method, and (c) 0.1 EU or less of pyrogen.

(4) Pharmaceutical preparation

The thus obtained rHSA (or a composition containing the same) can be made into a pharmaceutical preparation in accordance with known techniques such as ultrafiltration, sterile filtration, dispensing, lyophilization. Also, in order to ensure stability during its production steps and preservation stability after its production, acetyl tryptophan or a salt thereof (sodium salt for example) and sodium caprylate may be blended as stabilizing agents as occasion demands. These stabilizing agents may be used in an approximate amount of from 0.01 to 0.2M, preferably from 0.02 to 0.05M. The sodium content may be 3.7 mg/ml or less. These stabilizing agents may be added prior to the steps of ultrafiltration, sterile filtration, dispensing, lyophilization.

The rHSA pharmaceutical preparation thus obtained by ultrafiltration and sterile filtration is aseptically packed in a container in an administration unit. The term "packed in a container in an administration unit" as used herein means that an administration unit of the rHSA pharmaceutical preparation, for example, a liquid preparation containing 25% of rHSA having an approximate pH value of 6.4 to 7.4 and an osmotic pressure ratio of about 1, is packed in containers in 20 to 50 ml (5 to 12.5 g rHSA) portions; or it means that a liquid preparation containing 5% of the rHSA is packed in containers in 100 to 250 ml (5 to 12.5 g rHSA) portions. Examples of the container for use in the packing the rHSA pharmaceutical preparation include a glass container, a polyethylene container, a dealkalinized soft glass container (JP-A-4-210646), each having a capacity of 10 to 250 ml.

II. Heat treatment (pasteurization)

Though the rHSA pharmaceutical preparation thus obtained through the above steps seems to have an extremely low possibility of being contaminated with microorganisms, inactivation of contaminating microorganisms is carried out by pasteurization of the rHSA preparation after its aseptic packing, as a means to more positively ensure sterility of the preparation.

Contaminating microorganisms can be completely inactivated by pasteurization, by subjecting the pharmaceutical preparation packed in any of the aforementioned containers in an administration unit to at least 30 minutes, preferably 30 minutes to 2 hours, of incubation for example in a water bath controlled at a temperature of from 50° to 80° C., preferably at 60° C. Particularly preferred pasteurization is carried out at 60° C. for 30 minutes or at 60° C. for 1 hour.

The thus produced rHSA pharmaceutical preparation can be used clinically in injections in the same manner as the case of plasma-derived HSA pharmaceutical preparations. For example, it can be used for the purpose of increasing plasma quantity rapidly at the time of shock, supplementing circulatory blood volume, ameliorating hypoproteinemia and maintaining colloid osmotic pressure. Illustrative of its efficacy and effects, it is useful for the treatment of hypoalbuminemia and hemorrhagic shock caused by albumin loss, due, for example, to burns or nephrotic syndrome, and decreased albumin synthesis (hepatic cirrhosis).

With regard to its use and volume, 20 to 50 ml of 25% HSA solution or 100 to 250 ml of 5% solution (5 to 12.5 g HSA) is generally administered to an adult gradually by intravenous injection or intravenous drip infusion. The dose may be increased or decreased depending on the age, symptom and body weight of each patient.

Since microorganisms contaminating in an rHSA pharmaceutical preparation that is packed in a container in an administration unit die from the sterilization method of the present invention, rHSA pharmaceutical preparations having markedly high safety can be provided.

The following examples are provided to further illustrate the present invention. It is to be understood, however, that the examples are for purpose of illustration only and are not intended as a definition of the limits of the present invention.

EXAMPLE 1

Purified rHSA (or a composition containing the same) obtained in the Reference Example as described below was subjected to ultrafiltration using a ultrafiltration membrane having a molecular weight exclusive limit of about 30,000 and sterile filtration and packed aseptically in a 50 ml capacity glass automatic bottle, and the thus prepared pharmaceutical preparation was used in the following examples. In this instance, a control pharmaceutical preparation was also prepared by purifying HSA with no aseptic treatment and packing the purified HSA un-aseptically without employing sterile filtration.

(1) Preparation of cell suspension

Microbial strains used in the sterilization test are shown in Table 1. Strains with IFO numbers were obtained from Institute for Fermentation, Osaka.

TABLE 1

Microbial strains used

| Strain name | ATCC No. | IFO No. |
| --- | --- | --- |
| Escherichia coli | 8739 | 3972 |
| Pseudoinonas aeruginosa | 9027 | 13275 |
| Staphylococcus aureus | 6538 | 13276 |
| Candida albicans | 10231 | 1594 |
| Aspergillus niger | 16404 | 9455 |
| Pichia pastoris UHG 42-3 | | |
| Bacillus subtilis | 9372 | 13721 |

(a) Preparation of cell suspension

One loopful of cells of each of the above strains, except for the spore-containing cells of *Asp. niger*, were inoculated into 5 ml of SCD medium (SCD medium "Daigo", manufactured by Nippon Seiyaku) and cultured for 24 hours on a shaker (BR-30, manufactured by TAITEC). *E. coli, Ps. aeruginosa, Staph. aureus* and *B. subtilis* were cultured at 37° C., and *C. albicans* at 20° to 25° C. (room temperature) and *P. pastoris* at 30° C. After culturing, 2 ml of the culture mixture was transferred into a sterile centrifugation tube and centrifuged at 3,000 rpm for 10 minutes. The cells thus obtained as a pellet were washed by suspending them in 2 ml of physiological saline and subjecting the suspension to centrifugation. After repeating this washing step twice, the resulting cells were suspended in 2 ml of physiological saline to prepare a cell suspension.

In order to determine the inoculum size of each strain for the pasteurization test, cell suspensions, of each strain were diluted serially to measure turbidities of the dilutions at $OD_{610}$, and the dilutions were also inoculated onto SCD agar medium (SCD agar medium "Daigo", manufactured by Nippon Seiyaku) to find a relationship between $OD_{610}$ and viable count.

(b) Preparation of *Asp. niger* spore suspension

Spores and hyphae of *Asp. niger* were inoculated on SCD agar plate medium and cultured in a stationary position at 20° to 25° C. (room temperature) for 7 days or more. Several plates on which spores were sufficiently formed were prepared, and 5 to 10 ml of physiological saline containing 0.05% Tween 80 (polyoxyethylene (20) sorbitan monooleate, manufactured by ICI) was poured in each of the plates to recover the spores by suspending them with a pipette.

The spore suspension was passed through a sterile glass filter with suction to remove hyphae from the suspension and then a relationship between $OD_{610}$ and spore numbers was calculated in the same manner as described in the above step (a).

The relationship between $OD_{610}$ and viable count or spore numbers in each of the cell suspensions or spore suspension prepared above is shown in Table 2. A good linear relationship was observed between cell density (or spore numbers) and $OD_{610}$ when the $OD_{610}$ value was 0.3 or less. The inoculum size of each strain for the pasteurization test was determined based on the results shown in Table 2.

TABLE 2

Relationship between $OD_{610}$ and viable counts or spores

| Strain name | Viable counts or spores per $OD_{610} = 1$ (cells/ml) |
| --- | --- |
| Escherichia coli | $2.9 \times 10^8$ |
| Pseudomonas aeruginosa | $15.8 \times 10^8$ |
| Staphylococcus aureus | $3.6 \times 10^8$ |
| Candida albicans | $2.7 \times 10^7$ |
| Aspergillus niger (spores) | $3.5 \times 10^6$ |
| Pichia pastoris UHG 42-3 | $4.2 \times 10^7$ |
| Bacillus subtilis (vegetative cells) | $2.0 \times 10^8$ |

(2) Heat treatment test (pasteurization)

This test was carried out in accordance with USP XX II (1990) Microbiological Test (U.S. Pharmacopeia National Formulary XX II <51>, 1478 (1990)). A 0.25 ml portion of the cell suspension or spore suspension prepared in the above procedure (1) was inoculated into 50 ml of the 25% rHSA pharmaceutical preparation aseptically produced in the Reference Example to a density of 100,000 to 1,000,000 cells/ml rHSA preparation and stirred thoroughly, and, for use in the measurement of initial viable count, a 1 ml portion of the resulting mixture was sampled via a sampling port instead of the rubber-stopped upper inlet used for the inoculation in order to prevent cross contamination. Thereafter, heat treatment was carried out by submerging the container, except for its upper rubber stopper portion, in a hot water bath controlled at 60° C.

For use in the measurement of viable counts, the rHSA pharmaceutical preparation was periodically sampled in 1 ml portions in such a manner that the container was taken out of the both, followed by a thorough stirring, a sampling was taken out, and the container was quickly returned to the hot water bath. The samples were immediately cooled in a water bath controlled at 10° to 15° C. In order to measure viable count, each sample was diluted to an appropriate cell density with physiological saline, a 100 ml portion of the dilution was inoculated onto the SCD agar plate medium that was subsequently incubated in a stationary position for several days at a culture temperature corresponding to each strain, as described in (1), and then the number of colonies formed on the plate medium was counted. The results are shown in Table 3. As a control, another rHSA preparation that was not heated after inoculation of cells was also periodically sampled to measure changes in the viable count in the same manner as described above, with the results shown in Table 4. In these tables, the retention time in the hot water bath includes a period of about 12 minutes for the temperature at the central portion the rHSA pharmaceutical preparation to reach 60° C.

TABLE 3

Results of heat treatment test - 1

| Retention time in water bath (hr) | Viable count (cells/ml) | | | |
|---|---|---|---|---|
| | E. coli | Ps. aeruginosa | Staph. aureus | C. albicans |
| 0 | 30 × 10⁴ | 27 × 10⁴ | 40 × 10⁴ | 30 × 10⁴ |
| 0.25 | 260 | 0 | 200 | 0 |
| 0.5 | 0 | 0 | 0 | 0 |
| 1.0 | 0 | 0 | 0 | 0 |
| 1.5 | 0 | 0 | 0 | 0 |
| 2.5 | 0 | 0 | 0 | 0 |
| 3.5 | 0 | 0 | 0 | 0 |
| 5.5 | 0 | 0 | 0 | 0 |
| 7.5 | 0 | 0 | 0 | 0 |
| 11.25 | 0 | 0 | 0 | 0 |

Results of heat treatment test - 2

| Retention time in water bath (hr) | Viable Count (cells/ml) | | |
|---|---|---|---|
| | P. pastoris | Asp. niger (spores) | B. subtilis (vegetative cells) |
| 0 | 25 × 10⁴ | 26 × 10⁴ | 91 × 10⁴ |
| 0.25 | 0 | 0 | 0 |
| 0.5 | 0 | 0 | 0 |
| 1.0 | 0 | 0 | 0 |
| 1.5 | 0 | 0 | 0 |
| 2.5 | 0 | 0 | 0 |
| 3.5 | 0 | 0 | 0 |
| 5.5 | 0 | 0 | 0 |
| 7.5 | 0 | 0 | 0 |
| 11.25 | 0 | 0 | 0 |

TABLE 4

Results of no heat treatment test - 1

| Retention time in water bath (hr) | Viable count (cells/ml) | | | |
|---|---|---|---|---|
| | E. coli | Ps. aeruginosa | Staph. aureus | C. albicans |
| 0 | 58 × 10⁴ | 22 × 10⁴ | 52 × 10⁴ | 25 × 10⁴ |
| 0.5 | 95 × 10⁴ | 18 × 10⁴ | 36 × 10⁴ | 39 × 10⁴ |
| 1.5 | 17 × 10⁴ | 24 × 10⁴ | 58 × 10⁴ | 35 × 10⁴ |
| 3.5 | 63 × 10⁴ | 28 × 10⁴ | 43 × 10⁴ | 45 × 10⁴ |
| 5.5 | 77 × 10⁴ | 43 × 10⁴ | 56 × 10⁴ | 45 × 10⁴ |

Results of no heat treatment test - 2

| Retention time in water bath (hr) | Viable Count (cells/ml) | | |
|---|---|---|---|
| | P. pastoris | Asp. niger (spores) | B. subtilis (vegetative cells) |
| 0 | 29 × 10⁴ | 29 × 10⁴ | 61 × 10⁴ |
| 0.5 | 50 × 10⁴ | 21 × 10⁴ | 47 × 10⁴ |

TABLE 4-continued

| 1.5 | 40 × 10⁴ | 31 × 10⁴ | 73 × 10⁴ |
| 3.5 | 46 × 10⁴ | 25 × 10⁴ | 72 × 10⁴ |
| 5.5 | 54 × 10⁴ | 23 × 10⁴ | 51 × 10⁴ |

It was confirmed from the results shown in Table 4 that the rHSA pharmaceutical preparation itself has no germicidal activity against each strain tested. Also, as is evident from the results shown in Table 3, each of the strains inoculated into the rHSA pharmaceutical preparation completely dies out when the inoculated preparation is maintained for 30 minutes in a hot water bath controlled at 60° C.

EXAMPLE 2

In order to confirm more precisely the inactivation of each strain after 30 minutes or 1 hour of heat treatment at 60° C., a test was carried out in accordance with the sterility test (direct method, biological products standards) that is applied to pharmaceutical preparations of 100 ml or less in volume. The results are shown in Table 5.

TABLE 5

Results of sterility test

| Sample | Strains inoculated | Heating condition | Presence of viable cells |
|---|---|---|---|
| rHSA preparation purified under non-aseptic condition | none | no heating | yes |
| rHSA preparation purified under non-aseptic condition | none | 60° C., 30 min | no |
| rHSA preparation purified under non-aseptic condition | none | 60° C., 1 hr | no |
| rHSA preparation sterile-filtered and sterile-packed | 6 strains | 60° C., 30 min | no |
| rHSA preparation sterile-filtered and sterile-packed | 6 strains | 60° C., 1 hr | no |
| rHSA preparation sterile-filtered and sterile-packed | none | 60° C., 30 min | no |

The term "rHSA preparation purified under non-aseptic condition" as used in Table 5 means a preparation prepared in accordance with the rHSA-preparing procedure shown in the Reference Example, except that sterility of all conditions ranging from tools to techniques used in each purification step was not taken into consideration and the sterile filtration step thereafter was not employed. This attempt was made with the aim of obtaining an rHSA pharmaceutical preparation contaminated with indigenous microorganisms which are present in the current environment.

On the other hand, the term "rHSA preparation sterile-filtered and sterile-packed" as used in Table 5 means a preparation prepared in accordance with the rHSA-preparing procedure shown in the Reference Example in which sterility of all conditions ranging from tools to techniques used in each purification step was taken into consideration and the sterile filtration and subsequent aseptic packing were carried out in the usual way. This test was carried out using a preparation inoculated with a mixture of the 6 strains so far examined (E. coli, Ps. aeruginosa, Staph. aureus, C. albicans, P. pastoris and Asp. niger) and another preparation with no inoculation of these strains. Inoculum size of each strain was 120,000 cells per ml of rHSA preparation. In this instance, the heating time means a period of time starting from the commencement of the heating of rHSA preparation, without taking into account the period (about 12 minutes) for the temperature at the central portion of the rHSA preparation to reach 60° C.

According to the results of this example, environmental microorganisms considered to be contaminating during purification and the 6 strains tested can be sterilized completely by 30 minutes of heat treatment at 60° C., and these results coincided well with the results of heat treatment test carried out in the foregoing. In addition, generation of viable cells was not observed in the preparation without inoculation of strains when it was heat-treated.

REFERENCE EXAMPLE

Preparation of purified rHSA (or a composition containing the same)

I. Culturing a HSA producing host and production of HSA (1) Used strain, *Pichia pastoris* GCP101

A strain of *Pichia pastoris*, PC4130, obtained in accordance with the process disclosed in JP-A-2-104290, corresponding to EP-A-344459, was made by digesting the plasmid pPGP1, containing a transcription unit that is constructed so as to express HSA under the control of an AOX1 promoter, with NotI, and then substituting the resulting NotI-digested fragment for the AOX1 gene region of a *Pichia pastoris* strain GTS1115 (his4) (NRRL deposition number Y-15851). The strain does not grow well in a medium containing methanol as the carbon source (Mut⁻ strain) because of the deletion of the AOX1 gene.

The strain PC4130 was inoculated into 3 ml of YPD medium (1% yeast extract, 2% Bacto Peptone and 2% glucose). After 24 hours of culturing, the cells were inoculated into 50 ml of YPD medium so that the cell density should be adjusted to initial turbidity with an $OD_{540}$ of 0.1. After 3 days of culturing at 30° C., the resulting cells again were inoculated into 50 ml of YPD medium at an initial cell turbidity of 0.1 at $OD_{540}$. Thereafter, subculturing was repeated every 3 days in the same manner. After each subculturing, cells were diluted with sterile water and poured onto a 2% MeOH-YNBw/oa.a. plate (0.7% Yeast Nitrogen Base without Amino Acids, 2% methanol and 1.5% agar powder) in an inoculum size of $10^7$ cells/plate, followed by 5 days of culturing at 30° C. to judge the present/absence of colonies. Twenty colonies were found on the 2% MeOH-YNBw/oa.a. plate after 12 days of the successive subculturing. Mut⁻ strains can hardly grow on the 2% MeOH-YNBw/oa.a. medium while Mut⁺ strains can grow well. That is, the advent of a colony means that the strain acquired the capacity of increased methanol assimilation and thus a Mut⁺ strain was obtained. One of the thus obtained colonies was diluted appropriately with sterile water and spread onto a 2% MeOH-YNBw/oa.a. plate to isolate single colonies. One of the resulting single colonies was named GCP101.

(2) Culturing of the strain (First seed culture)

A 1 ml portion of the strain which had been frozen in glycerol was inoculated into a 1,000 ml baffled Erlenmeyer flask containing 200 ml of YPD medium (see Table 6) and cultured at 30° C. for 24 hours with shaking.

TABLE 6

Composition of YPD medium

| Components | Concentration (g/L) |
|---|---|
| Yeast extract | 10 |
| Peptone | 20 |
| Glucose | 20 |

(Second seed culture)

The first seed culture broth was inoculated into a 10 liter-jar fermentor containing 5 liters of YPD medium, and the second seed culturing was carried out at 30° C. for 24 hours with agitation and at an aeration rate of 5 liters per minutes. In the seed culturing, the pH of the medium was not controlled.

(Main culture)

The second seed culture broth was transferred into a 1,200 liter-fermentor containing 250 liters of a batch culture medium (see Table 7), and batch culturing was started with agitation and aeration. The agitation rate was controlled so that the level of dissolved oxygen in the medium was maintained at approximately 50 to 30% of the saturated dissolved oxygen concentration. When the glycerol in the batch culture medium was consumed, addition of a feeding medium (see Table 8) was started. Feeding rate of the medium was controlled using a computer in such a manner that methanol did not accumulate in the culture medium, thereby effecting a high density culturing. The medium pH was controlled at a fixed level of 5.85. An antifoam agent was added to the culture medium for defoamation.

TABLE 7

Composition of batch culture medium

| Components | Amount per liter |
|---|---|
| Glycerol | 50.0 g |
| $H_3PO_4$ (85%) | 14.0ml |
| $CaSO_4.2H_2O$ | 0.6 g |
| $K_2SO_4$ | 9.5 g |
| $MgSO_4.7H_2O$ | 7.8 g |
| KOH | 2.6 g |
| Biotin solution*¹ | 1.6ml |
| YTM solution*² | 4.4ml |
| $FeSO_4.7H_2O$ | 65.0 g |
| $CuSO_4.5H_2O$ | 6.0 g |
| $ZnSO_4.7H_2O$ | 20.0 g |
| $MnSO_4.4-5H_2O$ | 3.0 g |
| $H_2SO_4$ | 5.0ml |

*¹Biotin solution: 0.2 g/l
*²YTM solution:

TABLE 8

Composition of feeding medium

| Components | Amount |
|---|---|
| YTM solution | 2 ml |
| Methanol | 1,000 ml |

An HSA expression plasmid pMM042 was constructed using an AOX2 promoter (a mutant of the natural AOX2 promoter (*YEAST*, 5, 167–177, 1988; *Mol. Cell. Biol.*, 9, 1316–1323, 1989), in which the 255th base upstream from the initiation codon of said promoter is changed from T to C) isolated from the above-described strain GCP101. The thus constructed plasmid was introduced into *Pichia pastoris* GTS1115 to obtain a transformant UHG42-3 (JP-A-4-299984 or EP-A-506040). Thereafter, the thus obtained transformant was cultured in accordance with the above procedure, thereby allowing the transformant to produce HSA.

II. Purification (high grade) of HSA (1) Isolation of culture supernatant—membrane fractions (I) and (II)

About an 800 liter portion of the culture broth obtained in the above procedure was subjected to a filter press to isolate the culture supernatant. The resulting supernatant subsequently was passed through an ultrafiltration membrane having a molecular weight exclusive limit of 300,000. Then, the resulting filtrate was concentrated to a volume of about 80 liters using an ultrafiltration membrane having a molecular weight exclusive limit of 30,000 (membrane fraction (I)).

Next, the membrane fraction (I) was heat-treated at 60° C. for 3 hours in the presence of 5 mM of sodium caprylate, 10 mM of cysteine and 100 mM of aminoguanidine at pH 7.5. The thus heat-treated solution was cooled down rapidly to about 15° C., adjusted to pH 4.5 and then treated with an ultrafiltration membrane having a molecular weight exclusive limit of 300,000 (membrane fraction (II)). Thereafter, using an ultrafiltration membrane having a molecular weight exclusive limit of 30,000, the buffer in the resulting albumin solution was replaced by a 50 mM acetate buffer (pH 4.5) containing 50 mM of sodium chloride.

(2) Cation exchanger treatment

The albumin solution obtained in the above step (1) was applied to a column packed with S-Sepharose that had been equilibrated in advance with a 50 mM acetate buffer (pH 4.5) containing 50 mM of sodium chloride, the column was washed thoroughly with the same buffer and then elution was carried out with a 0.1M phosphate buffer (pH 9) containing 0.3M sodium chloride.

(3) Hydrophobic chromatography

The HSA solution eluted from the S-Sepharose column was applied to a column packed with Phenyl Cellulofine which had been equilibrated in advance with a 50 mM phosphate buffer (pH 6.8) containing 0.15M sodium chloride. Since HSA does not adsorb to Phenyl Cellulofine under such conditions, the HSA fractions that passed through the column were collected. The HSA solution thus recovered was concentrated to a volume of about 50 liters using an ultrafiltration membrane having a molecular weight exclusive limit of 30,000, and at the same time, the buffer in the HSA solution was replaced by a 50 mM phosphate buffer (pH 6.8).

(4) Anion exchanger treatment

The HSA solution thus treated with hydrophobic chromatography, concentrated and buffer-exchanged was applied to a column packed with DEAE-Sepharose which had been equilibrated in advance with a 50 mM phosphate buffer (pH 6.8). Under such conditions, HSA was not adsorbed to the DEAE-Sepharose but passed through the column.

(5) Decoloration

A 1 ml portion of the 25 w/v % solution of purified HSA was mixed with 1 g of DIAION CRB02 (a chelate resin having a styrene-divinylbenzene copolymer as the carrier portion and an N-methylglucamine group as the ligand portion, manufactured by Mitsubishi Kasei Corp.), and the resulting mixture was stirred for 24 hours at room temperature at pH 6.8 and ionic strength of 5 mmho. The resin then was washed with distilled water to recover the non-absorbed HSA-containing fraction.

(6) Hydrophobic chromatography

Sodium chloride was added to the HSA-containing solution to a final concentration of 0.5M. The resulting solution was adjusted to a pH of 3.5 and applied to a column packed with Phenyl-Cellulofine. The column was washed with a 0.5M sodium chloride solution (pH 3.5) and elution was carried out using 50 mM phosphate buffer (pH 6.8) containing 0.15M sodium chloride.

(7) Borate treatment

The HSA concentration of the HSA-containing solution was adjusted to 2.5 w/v % so that the electric conductivity became 1 mS or below. Calcium tetraborate was added to the resulting solution to a final concentration of 100 mM and a pH value of the solution was adjusted to 9.5. After allowing the solution to stand for 10 hours, the precipitate formed was removed to recover the supernatant, which was then concentrated and desalted.

(8) Ultrafiltration

The thus-recovered HSA-containing solution was passed through a ultrafiltration membrane having a molecular weight exclusive limit of about 100,000.

III. Properties of purified rHSA (or a composition containing the same)

(1) HPLC analysis of purification steps

HSA was analyzed by HPLC gel filtration. The gel filtration analysis was carried out under the following conditions. Column: TSK gel G3000SW (manufactured by Tosoh) Developing solution: $0.1M$ $KH_2PO_4/0.3M$ NaCl buffer Detection: absorbance at a wave length of 280 nm The purified HSA-containing composition showed a single peak of HSA monomer.

(2) Analysis of yeast-derived components

A culture supernatant of an HSA non-producing yeast was partially purified in the same manner as described above and the resulting HSA-containing composition was used to immunize rabbits. Using the thus-obtained antiserum, detection of yeast-originated components in the purified HSA-containing composition was carried out by means of enzyme immunoassay (EIA).

Results of the detection of yeast-derived components in each sample are shown in Table 9. The measurement was carried out by adjusting the HSA concentration of each sample to 250 mg/ml.

(3) Molecular weight

The above-mentioned HPLC gel filtration analysis was employed for the measurement of molecular weight. Molecular weight of HSA in the purified HSA-containing composition of the present invention was found to be about 67,000, which was almost the same as that of plasma-derived HSA.

(4) Isoelectric point

The isoelectric point was measured in accordance with the procedure of Allen et al. (*J. Chromatog.*, 146, 1 (1978)) using thin layer polyacrylamide gel electrophoresis. The isoelectric point of HSA in the purified HSA-containing composition of the present invention was found to be about 4.9 which was almost the same as that of plasma-derived HSA.

(5) Degree of coloring

Absorbances at 280 nm, 350 nm, 450 nm and 500 nm were measured to calculate the degree of coloring as $A_{350}/A_{280}$, $A_{450}/A_{280}$ and $A_{500}/A_{280}$. The degree of coloring of the purified HSA-containing composition of the present invention was found to be about 0.02 as $A_{350}/A_{280}$, about 0.01 as $A_{450}/A_{280}$ and about 0.002 as $A_{500}/A_{280}$, which was almost the same as that of plasma-derived HSA.

(6) Linked fatty acid content

NFEA-Test Wako (manufactured by Wako Pure Chemical Industries) was used for the measurement. The fatty acid content was 1.6 moles (per mole HSA) before the chelate resin treatment, but sharply decreased to 0.037 mole (per mole HSA) after the treatment.

(7) Determination of the content of free contaminants by the phenol-sulfuric acid method The content of free contaminants in each HSA fraction was determined by the phenol-sulfuric acid method in the conventional manner. Thus, each HSA fraction was directly examined by the phenol-sulfuric acid method to determine the total content of the contaminants, that is, the sum of the free contaminant content and the nonfree contaminant content. Separately, each HSA fraction was treated with ConA-Sepharose (Pharmacia) in the same manner as described above and non-adsorbed fractions containing HSA were subjected to the phenol-sulfuric acid method to determine the content of nonfree contaminants. The difference obtained by taking the latter from the former means the content of free contaminants. A standard curve was prepared using mannnan as a standard material. The results are shown in Table 9.

(8) Measurement of pyrogen

The measurement was carried out using Endospecy manufactured by Seikagaku Corporation.

TABLE 9

| | | Contaminants (per 250 mg HSA) | | |
|---|---|---|---|---|
| Sample No. | HSA recovery | EIA | Phenol-sulfuric acid method (free body) | Pyrogen (per 250 mg HSA) |
| 1 After decoloration | — | 10 ng | 700 ng | 2.9 EU |
| 2 After borate treatment | ≧95% | <0.1 ng | <1 μg | — |
| 3 After ultrafiltration | ≧95% | <0.1 ng | <1 μg | <0.1 EU |

The purified rHSA (or composition containing the same) thus obtained has markedly high purity because of success in removing a sufficient quantity of contaminants from the HSA-containing fraction, such as certain contaminants originating from the medium and substances contained in or secreted by the microorganism (producer host), particularly host-derived contaminants having antigenicity, non-antigenic free contaminants detectable by phenol-sulfuric acid method and pyrogens (exothermic substances).

While the instant invention has been described in detail and with reference to specific embodiments thereof, it will be apparent to one skilled in the art that various changes and modifications can be made therein without departing from the spirit and scope thereof.

What is claimed is:

1. A method for preparing a sterilized recombinant human serum albumin pharmaceutical preparation, comprising subjecting a pharmaceutical preparation of recombinant human serum albumin, which is packed in a container in an administration unit, to heat treatment at 50° to 80° C. for 30 minutes to 2 hours.

2. The method of claim 1, wherein the pharmaceutical preparation of recombinant human serum albumin is subjected to heat treatment at 60° C. for 30 minutes to 2 hours.

3. The method of claim 1, which comprises:

(1) heat-treating a culture supernatant containing recombinant human serum albumen in order to inactivate contaminant proteases in the supernatant; and thereafter (2) subjecting the pharmaceutical preparation of the recombinant human serum albumin, which is packed in the container in the administration unit, to heat treatment at 50° to 80° C. for 30 minutes to 2 hours.

4. The method of claim 3 wherein step (1) is carried out at a temperature of 50° to 70° C. for 30 minutes to 5 hours.

5. The method of claim 3, wherein contaminant microorganisms are sterilized in step (2).

6. The method of claim 5, wherein the contaminant microorganisms are selected from the group consisting of *Escherichia coli, Pseudomonas aeruginosa, Staphylococcus aureus, Candida albicans, Aspergillus niger, Pichia pastoris* and *Bacillus subtilis*.

* * * * *